United States Patent [19]

Smolnikov et al.

[11] 4,222,386
[45] Sep. 16, 1980

[54] METHOD FOR STIMULATING CARDIAC ACTION BY MEANS OF IMPLANTED ELECTROCARDIOSTIMULATOR AND IMPLANTABLE ELECTROCARDIOSTIMULATOR FOR EFFECTING SAME

[76] Inventors: Leonid E. Smolnikov, ulitsa Baikalskaya, 47, kv. 29; Boris A. Ivobotenko, Beshilovskaya ulitsa, 17, kv. 34; Adrian B. Aparov, Krasnokazarmennaya ulitsa, 12, korpus 3, kv. 50; Valery I. Shumakov, Smolenskaya ulitsa, 7, kv. 56; Jury I. Abasheev, Energeticheskaya ulitsa, 8, korpus 1, kv. 130; Mikhail M. Isachenko, Vyatskaya ulitsa, 3, kv. 12, all of Moscow; Vladimir N. Korolev, ulitsa Zavodskaya, 7, kv. 12, Klimovsk-1 Moskovskoi oblasti, all of U.S.S.R.

[21] Appl. No.: 24,048

[22] Filed: Mar. 26, 1979

Related U.S. Application Data

[63] Continuation of Ser. No. 888,525, Mar. 21, 1978, abandoned.

[51] Int. Cl.² .............................................. A61N 1/36
[52] U.S. Cl. ............................................. 128/419 PG
[58] Field of Search ..................... 128/419 P, 419 PG

[56] References Cited

U.S. PATENT DOCUMENTS

| 3,683,934 | 8/1972 | Bukowiecki et al. | 128/419 PG |
| 3,920,024 | 11/1975 | Bowers | 128/419 PG |
| 3,939,844 | 2/1976 | Pequignot | 128/419 PG |

*Primary Examiner*—William E. Kamm
*Attorney, Agent, or Firm*—Fleit & Jacobson

[57] ABSTRACT

A method for stimulating the cardiac action by means of an electrocardiostimulator implanted in the patient's body and connected to the heart, ensuring a desired heart rate, whereby a packet of electric pulses is produced, the number of heart contractions being equal to the number of pulse packets applied to the heart in the presence of stimulating actions. The implantable electrocardiostimulator comprises a main pulse generator connected to a power source and associated with the heart through electrodes, as well as an auxiliary pulse generator connected between said main pulse generator and electrodes. The natural frequency of pulses produced by said auxiliary generator is higher than the repetition frequency of pulses produced by the main generator.

5 Claims, 4 Drawing Figures

METHOD FOR STIMULATING CARDIAC ACTION BY MEANS OF IMPLANTED ELECTROCARDIOSTIMULATOR AND IMPLANTABLE ELECTROCARDIOSTIMULATOR FOR EFFECTING SAME

This is a continuation of application Ser. No. 888,525, filed Mar. 21, 1978 now abandoned.

The present invention relates to medicine and is applicable to the treatment of cardiac rhythm disturbances in cases drug therapy proves to be ineffective.

There is known a method for acting upon the heart by means of an electrocardiostimulator implanted in the patient's body and connected to the heart; there is further known an implantable electrocardiostimulator for carrying out this method (cf. U.S. Pat. No. 3,057,356, Cl. 128-422).

According to the above method, the electrocardiostimulator produces a continuous rectangular electric pulse with a duration of $T_o$, which is applied to the heart and makes it contract. The stimulator itself is a pulse generator, for example, a multivibrator or a self-oscillating flip-flop; its input is connected to a power source, whereas its output is connected via electrodes to the heart. The number of heart contractions corresponds to the number of pulses applied to the heart.

In order to stimulate the heart effectively, the duration of the pulse applied to the heart must be in excess of a certain threshold value. In the course of stimulation, the pulse repetition period T is always much greater than the pulse duration $T_o$ ($T/T_o = 600-1600$).

The foregoing method of heart stimulation is disadvantageous in that the electrocardiostimulator intended to realize this method requires a great power input, which affects the service life of the device.

With standard continuous pulse voltages of 5.2 V or 6.5 V (the amplitude value), the threshold duration for most patients is 0.05 to 0.2 msec.

To ensure reliable operation of the stimulator, the pulse duration is selected within the range of 0.5 to 1.5 msec, which means it is several times the threshold duration.

Consider the most typical case when a continuous pulse is applied to the heart at $T_o = 0.8$ msec. The pulse repetition period is 833 msec (72 heartbeats per minute); the heart resistance is 500 ohms (the typical value); the pulse voltage is 5.2; the stimulator's efficiency is 80 percent. In this case, the power intake of the heart is 52 muw; the power source output is 65 muw; and the source produces a current of 12.5 mua.

Thus with the use of a continuous pulse, the power source output must not be below 10 to 15 mua if the stimulation is to be maintained. The capacity of batteries incorporated in the power source is limited to 0.5 or 1.0 amp.-hr.; hence, the life of stimulators is largely determined by the power demand: the greater the current, the shorter the life of the stimulator.

The capacity of the existing batteries is such that the service life of all the conventional electrocardiostimulators is limited to a few years.

It is the main object of the present invention to reduce the input current value, while maintaining an effective stimulation, and thus prolong the service life of stimulators powered by conventional batteries.

It is another object of the invention to reduce the mass, size and cost of stimulators without affecting their service life span.

The foregoing and other objects of the present invention are attained by providing a method for stimulating the cardiac action by means of an electrocardiostimulator implanted in the patient's body and connected to the heart, whereby a pulse packet is produced to be applied to the heart so as to make it contract, the stimulation being such that the number of heart contractions is equal to that of pulse packets applied to the heart.

With the use of the proposed method, the stimulation threshold is decreased several times; as a result, the service life of implanted electrocardiostimulators is increased several times, although they employ conventional power sources, and their mass and size remain unchanged.

The method of this invention is preferably carried out with the use of an implantable electrocardiostimulator comprising a main pulse generator intended to set the cardiac rhythm and connected to a power source; the stimulator further includes an output switch connected to the heart, a power circuit breaker, and an auxiliary pulse generator electrically interposed between the main pulse generator and the switch and connected via the power circuit breaker to said power source, the natural frequency of said auxiliary pulse generator being greater than that of said main pulse generator.

The proposed design of an implantable electrocardiostimulator provides for a considerable prolongation of the service life of such an electrocardiostimulator and makes it possible to use the redundant power to put into action auxiliary units of new types of stimulators with are becoming increasingly sophisticated from the viewpoint of their functional potentialities, as well as increasingly adaptable to the human organism.

To ensure a desired heart rate, the main pulse generator may include a clock circuit composed of a capacitor and resistor in series, as well as a discharge unit; the central tap of said circuit is connected to the input of the discharge unit, whereas the output of the discharge unit is connected to said auxiliary generator.

To ensure desired parameters of a pulse packet, the auxiliary pulse generator may be constructed as a multivibrator, whereto an output switch is connected. The latter's output may be connected to the heart directly or via electrodes.

In its simplest form, the output switch is a transistor operating as a pulse power amplifier and an isolation element.

To ensure a maximum safety of the patient, the output switch is constructed as a circuit including a resistor and a transistor placed in series, as well as an output separation capacitor connected to the central tap of said circuit.

Other objects and advantages of the present invention will become more apparent from the following detailed description of preferred embodiments thereof, taken in conjunction with the accompanying drawings, wherein.

Figure 1:
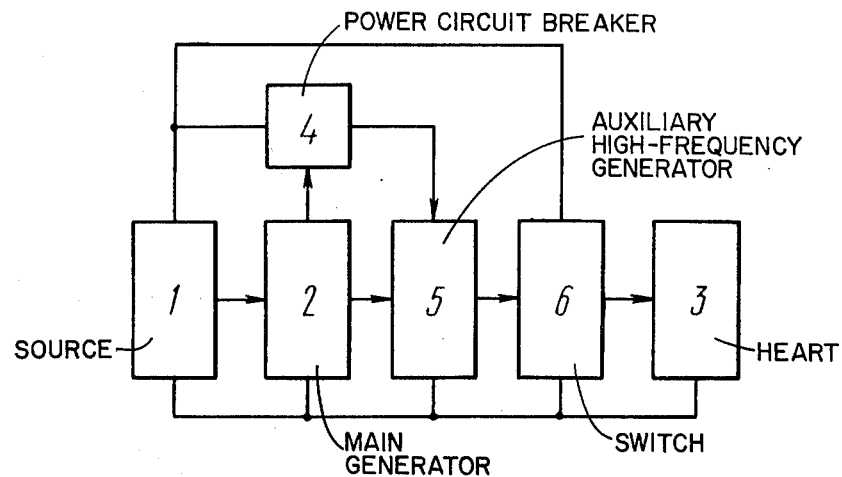
FIG. 1 is a block diagram of an implantable electrocardiostimulator connected to the heart, in accordance with the invention.

The proposed method for stimulating the cardiac action with the aid of an implanted electrocardiostimulator will be dealt with in detail in the following description of the design and operation of the stimulator intended for carrying out the method of this invention.

The proposed electrocardiostimulator comprises a power source 1 (FIG. 1), whereto is connected a main generator 2 intended to set the rate of a heart 3. One of the outputs of the main generator 2 is connected to the input of a power circuit breaker 4 which is electrically interposed between the power source 1 and an auxiliary high-frequency generator 5. In its turn, the auxiliary generator 5 is connected to the input of a switch 6 intended to control the heart 3.

The electrocardiostimulator of FIG. 1 operates as follows.

Figure 2:
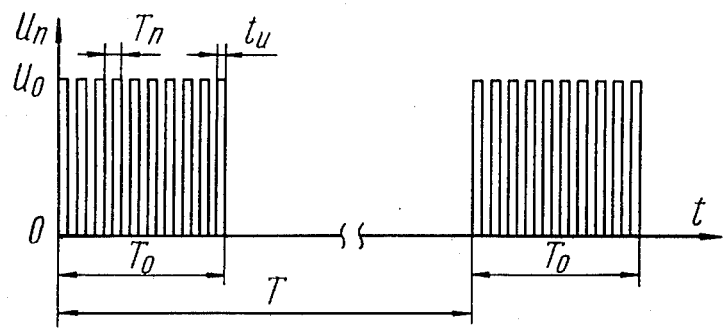
FIG. 2 shows a pulse packet used to stimulate the heart, in accordance with the invention.

The source 1 powers the main generator 2 which forms unipolar rectangular pulses. The power circuit breaker 4 is closed only for a period of time equal to the duration of the pulse produced by the main generator 2. Power is supplied to the auxiliary high-frequency generator 5 through the breaker 4; the auxiliary generator 5, too, operates only within periods of time equal to the duration of pulses produced by the main generator 2; the auxiliary generator 5 forms packets of electric pulses applied to the heart 3 via the output switch 6. FIG. 2 shows the relationship between the output voltage $U_n$ of the electrocardiostimulator (FIG. 1) and time t. In FIG. 2, $T_o$ is the duration of a pulse packet; $t_u$ is the duration of a pulse in the packet; $T_n-t_u$ is the duration of an interval between pulses in the packet; $T_n$ is the pulse repetition period in the packet; T is the repetition period of pulse packets; and $U_o$ is the amplitude of pulses in a packet.

Figure 3:
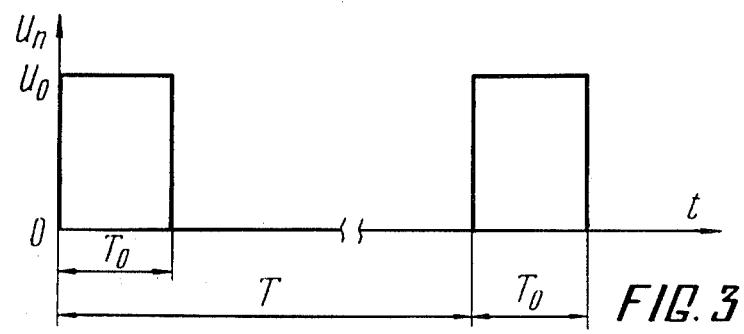
FIG. 3 shows a continuous pulse used to stimulate the heart in accordance with the known method.

For comparison, FIG. 3 shows the relationship between the output voltage $U_o$ of the electrocardiostimulator and the time t, which is typical of the known method. In FIG. 3, $T_o$ is the duration of a continuous pulse; T is the pulse repetition period; and $U_o$ is the amplitude of pulses.

The output switch 6 performs a double function. First, it provides for galvanic isolation of the heart 3 from the auxiliary generator 5; second, it amplifies the power of the signal produced by the auxiliary generator 5.

The heart stimulation power threshold is known to be dependent upon the shape of pulses acting upon the heart; the stimulation power threshold can be reduced by changing a continuous pulse for a pulse packet.

According to the proposed method, the packet of electric pulses shown in FIG. 2 acts upon the heart 3 and makes it contract; the number of heart contractions is equal to that of pulse packets applied to said heart 3. The use of a packet of pulses instead of the continuous pulse shown in FIG. 3 makes it possible to reduce the power demand several times, while keeping the effectiveness of the stimulation at a desired level; as a result, the service life of the electrocardiostimulator is several times longer than it used to be. This is the basic advantage of the proposed method over the known one.

It is advisable that a pulse packet should be composed of rectangular pulses; under such conditions, the units of the stimulator operate in a switch-like mode, so the losses are kept at a minimum. It is further advisable that within a packet, the ratio between the interval duration $(T_n-t_u)$ and the pulse duration $t_u$ must be greater than 0.2; at a lesser ratio, it is impossible to have a marked gain in power.

Figure 4:
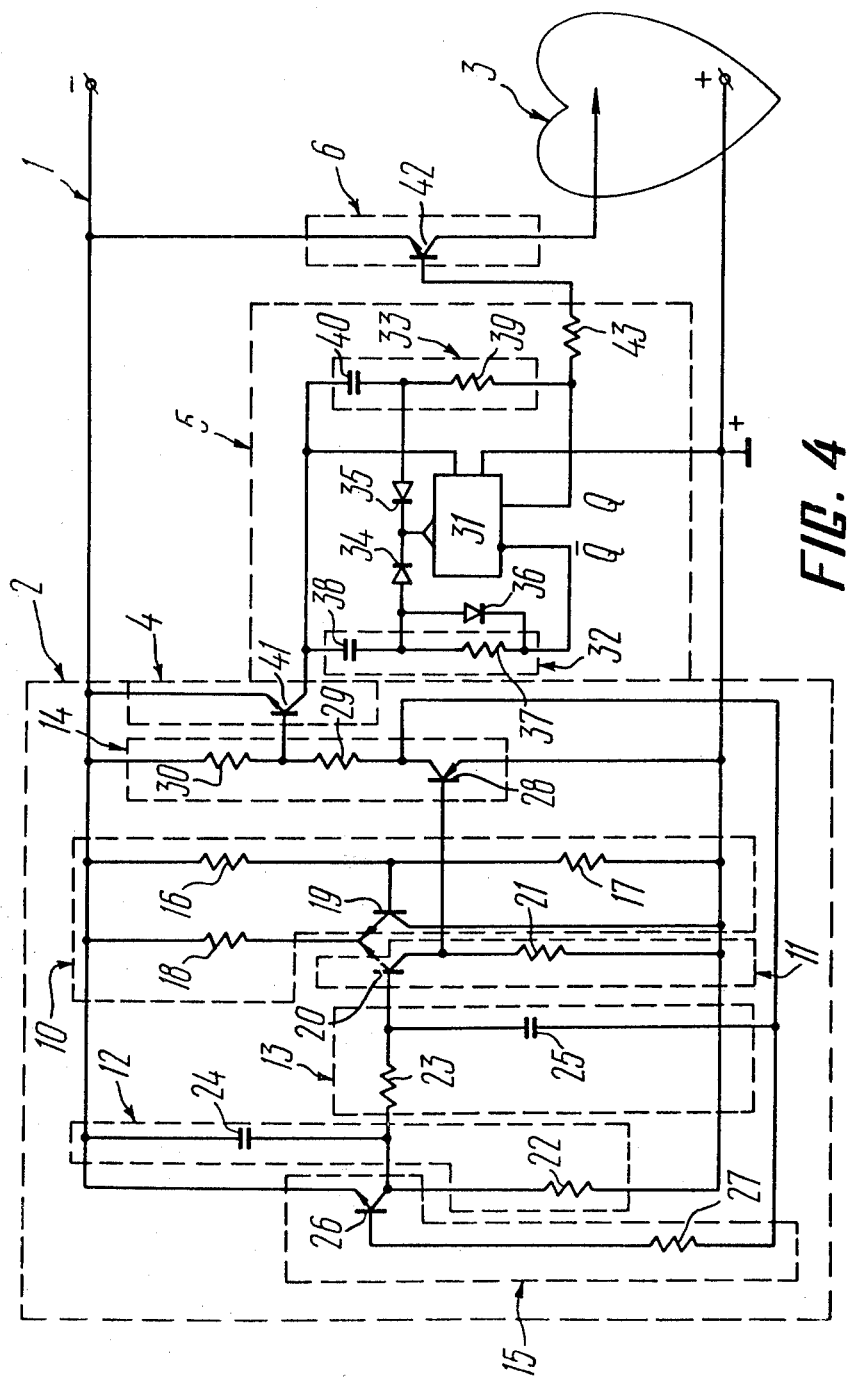
FIG. 4 is a key diagram of a preferred embodiment of implantable electrocardiostimulator in accordance with the invention.

The key diagram of FIG. 4 is related to the simplest, asynchronous, version of the proposed electrocardiostimulator.

The main pulse generator 2 comprises a reference voltage source 10, a comparator 11, and two RC circuits 12 and 13 intended to set the repetition period T of pulse packets and the packet duration $T_o$, respectively; the main pulse generator 2 further includes an intermediate transistor amplifier 14 and a discharge unit 15.

The reference voltage source 10 is built around resistors 16, 17 and 18 and a transistor 19. The comparator 11 is built around a transistor 20 and a resistor 21. The RC circuits 12 and 13 are built around resistors 22 and 23 and capacitors 24 and 25, respectively. The discharge unit 15 is built around a transistor 26 and a resistor 27. The intermediate transistor amplifier 14 is built around a transistor 28 and resistors 29 and 30.

The basic element of the auxiliary high-frequency generator 5 is a flip-flop 31; the generator 5 also includes two RC circuits 32 and 33, intended for setting the pulse duration $t_u$ and the repetition period $T_n$ of pulses within a packet, respectively, as well as isolation diodes 34, 35 and 36. The RC circuit 32 is built around a resistor 37 and a capacitor 38. The RC circuit 33 is built around a resistor 39 and a capacitor 40.

The output switch 6 comprises a transistor 42 and a resistor 43. To ensure a maximum safety of the patient, the output switch 6 may be a circuit connected to the power source and composed of a resistor and an output switching transistor, placed in series, as well as an isolation capacitor connected to the central tap of the circuit.

The electrocardiostimulator of FIG. 4 operates as follows. As the transistor 19 of the main generator 2 is driven into conduction, the transistors 20, 26, 28, 41 and 42 are rendered non-conducting. With the non-conducting transistor 41, the power supply circuit of the auxiliary generator 5 is broken; the auxiliary generator 5 is in the off state, and no stimulating pulse is applied to the heart 3. As the transistor 20 conducts current, the capacitor 24 of the clock circuit 12 is charged through the resistor 22. As soon as the capacitor 24 is charged to a voltage level roughly equal to the voltage drop across the resistor 18 of the referency voltage source 10, the transistor 20 of the comparator 11 is driven into conduction, whereas the transistor 19 is rendered non-conducting. As this takes place, the transistors 26, 28 and 41 are driven into conduction, and voltage of the power source is applied via the breaker 4 to the auxiliary generator 5. At the same time the capacitor 24 is discharged through the discharge unit 15 (the transistor 26), while the capacitor 25 of the clock circuit 13 is re-charged. The re-charging time of the capacitor 25 determines the time during which the transistor 41 of the breaker 4 conducts current; hence, it determines the time of operation of the auxiliary generator 5 which produces a packet of stimulating pulses.

The auxiliary generator 5 operates as follows. As power is supplied to it through the breaker 4, the flip-flop 31 is in one of its stable states, for example, "1". As a result, there is a high potential at the output Q and a low potential at the output Q of said flip-flop 31. Under such conditions, the capacitor 40 of the clock circuit 33, which is connected via the diode 35 to the counting input of the flip-flop 31, is charged, whereas the capacitor 36 id discharged. Simultaneously, gate current is applied via the resistor 43 to the base of the transistor 42 of the switch 6; as a result, a single pulse of a packet with a duration of $t_u$ (FIG. 2) is formed in the collector circuit of said transistor 42. As voltage across the capacitor 40 reaches a trigger level, and the flip-flop 31 is reset so that there is a high potential at the output Q and a low potential at the output Q̄. As this takes place, the capacitor 38 is charged, while the capacitor 40 discharges. At this stage the transistor 42 is off, and an interval with a duration of $(T_n-t_u)$ is formed within the packet. As voltage across the capacitor 38 reaches a trigger level, the flip-flop 31 is set again, whereupon the above sequence of events is repeated.

The working frequency of the auxiliary generator 5 is selected to be higher than the natural frequency of the main generator 2, so at the output of the stimulator there are produced packets of pulses with a certain time interval between them, as shown in FIG. 2.

The electrocardiostimulator of the present invention produces electric stimuli in the form of pulse packets and applies these packets to the heart. The greater the ratio between the frequencies of the main and auxiliary generators and the duty ratio within a packet, the greater the power gain and the longer the service life of the stimulator.

The power demand of the asynchronous stimulator described above is twice as low as that of electrocardiostimulators of the known type. As a result, the service life of the proposed stimulator is twice as long as that of prior-art stimulators.

The method and electrocardiostimulator design of the present invention are applicable to practically all types of implantable electrocardiostimulators, such as asynchronous, R-wave, P-wave, of the double stimulation type, etc., and invariably guarantee a gain in power.

What is claimed is:

1. A method for stimulating the cardiac action by means of a self-contained electrocardiostimulator implanted in the patient's body and connected to the heart, comprising the steps of: producing a signal having a plurality of packets, each said packet having a plurality of separate electric pulses each pulse being of a size insufficient to cause the heart to contract and having an interval therebetween; applying said signal having said packet of pulses to the heart to make it contract, such that the number of heart contractions is equal to the number of packets applied to the heart, thereby lessening the amount of power contained in each of said packets when compared to a single pulse of amplitude and duration equal to said packet.

2. The method of claim 1, further comprising the step of producing each of said separate electric pulses in said packet of pulses in the form of a rectangle.

3. A method as claimed in claims 1 or 2 comprising the further step of forming said packet of pulses such that the ratio between the interval between said separate electric pulses and the pulse width thereof within a pulse packet is selected to be greater than 0.2.

4. An implantable electrocardiostimulator intended to stimulate the cardiac action and comprising: a power source; a main pulse generator intended to set the heart rate and connected to said power source; an auxiliary generator intended to produce packets formed of individual high-frequency pulses and connected to said main generator; a power circuit breaker having two inputs and an output; the first of said two inputs of said power circuit breaker being connected to said power source; the second of said two inputs of said power circuit breaker being connected to said main generator; the output of said power circuit breaker being connected to the input of said auxiliary generator; and means connected to receive said packets of high-frequency pulses for supplying said packets of pulses to the heart.

5. An implantable electrocardiostimulator comprising:
   a power source;
   a main pulse generator containing a reference voltage source connected to said power source; a comparator connected to said reference voltage source; a first RC clock circuit determining the duration of said pulse packet and connected to said comparator; a second RC clock circuit determining the repetition period of said pulse packets; a discharge unit connected to the capacitor of said second RC clock circuit; an intermediate amplifier built around a transistor and connected to said comparator;
   a power circuit breaker built around a transistor and connected to the output of said intermediate amplifier and to said power source;
   an auxiliary generator connected via said power circuit breaker to said power source and including a flip-flop connected to said power circuit breaker; a first RC clock circuit determining the duration of the interval within said pulse packet and connected to said flip-flop; a second RC clock circuit determining the duration of a pulse in said pulse packet and connected to said flip-flop;
   an output switch built around a transistor and connected with its input to said flip-flop and with its output, via the heart, to said power source.

* * * * *